United States Patent [19]
Shulze

[11] Patent Number: 6,056,721
[45] Date of Patent: May 2, 2000

[54] BALLOON CATHETER AND METHOD

[75] Inventor: John E. Shulze, Rancho Santa Margarita, Calif.

[73] Assignee: Sunscope International, Inc., Newport Beach, Calif.

[21] Appl. No.: 08/907,718

[22] Filed: Aug. 8, 1997

[51] Int. Cl.⁷ ................................................. A61M 29/00
[52] U.S. Cl. ......................... 604/102; 604/101; 604/509; 600/194; 600/198; 600/191
[58] Field of Search .................................. 604/49, 52, 53, 604/96, 101, 103, 104, 102; 606/191, 192, 194, 198; 600/116

[56] References Cited

U.S. PATENT DOCUMENTS

| | | |
|---|---|---|
| 4,423,725 | 1/1984 | Baran et al. |
| 4,445,892 | 5/1984 | Hussein et al. |
| 4,573,966 | 3/1986 | Weikl et al. |
| 4,610,662 | 9/1986 | Weikl et al. |
| 4,636,195 | 1/1987 | Wolinsky |
| 4,824,436 | 4/1989 | Wolinsky |

(List continued on next page.)

FOREIGN PATENT DOCUMENTS

| | | |
|---|---|---|
| WO 90/07352 | 7/1990 | WIPO |
| WO 95/11719 | 5/1995 | WIPO |
| WO 95/26773 | 10/1995 | WIPO |
| WO 95/26777 | 10/1995 | WIPO |
| WO 96/19255 | 6/1996 | WIPO |

OTHER PUBLICATIONS

"Pharmacomechanical Thrombolysis in the Peripheral Vasculature (Pulse–Spray Technique)" Bookstein et al.; *Thrombolytic Therapy for Peripheral Vascular Disease;* 1995; pp. 297–311.

"Catheter–Based Techniques of Local Drug Delivey" McKay; *Manual of Interventional Cardiology;*pp. 645–60.

"Treatment of Intracoronary Thrombus with Local Urokinase Infusion Using a New, Site–Specific Drug Delivery System: The Dispatch™ Catheter" McKay et al.; *Catheterization and Cardiovascular Diagnosis* 33:181–88 (1994).

"Treatment of Acute Stent Thrombosis with Local Urokinase Trherapy Using Catherter–Based, Drug Delivery Systems: A Case Report" Mitchel et al.; *Catheterization and Cardiovascular Diagnosis* 34:149–54 (1995).

"Local Delivery of r–Hirudin by a Double–Baloon Perfusion Catheter Provents Mural Thrombosis and Minimizes Platelet Deposition After Angioplasty" Meyer et al.; *Circulation;* vol. 90, No. 5; Nov. 94; pp. 2474–80.

"Pharmacomechanical Thrombolysis with Urokinase for Treatment of Thrombosed Hemodialysis Access Grafts—A Comparison with Surgical Thrombectomy" Sands et al.; pp. 1–3.

"Management fo Hemodialysis Access Failure" Sands; pp. 1–8.

*Primary Examiner*—Wynn Wood Coggins
*Assistant Examiner*—Eric Kline
*Attorney, Agent, or Firm*—Stout, Uxa, Buyan & Mullins, LLP; Donald E. Stout

[57] ABSTRACT

A balloon catheter device for treating an obstructing material within a vascular conduit or other body passageway. The device comprises an elongate catheter body extending between a proximal end and a distal end. A high compliance balloon and a spaced apart angioplasty balloon are coaxially disposed along the distal end. The catheter device includes a plurality of longitudinal lumens which extend along the catheter body from the proximal end. At least one of the lumens has a cross section which is non circular and is configured, in conjunction with the other lumens to provide a maximum total lumen cross sectional area within a minimum diameter catheter body.

19 Claims, 4 Drawing Sheets

U.S. PATENT DOCUMENTS

| | | |
|---|---|---|
| 4,832,688 | 5/1989 | Sagae et al. . |
| 4,911,163 | 3/1990 | Fina . |
| 4,913,701 | 4/1990 | Tower .................................... 604/103 |
| 4,930,496 | 6/1990 | Bosley, Jr. ................................ 128/24 |
| 4,994,033 | 2/1991 | Shockey et al. . |
| 5,049,132 | 9/1991 | Shaffer et al. . |
| 5,059,178 | 10/1991 | Ya .......................................... 604/101 |
| 5,163,906 | 11/1992 | Ahmadi ................................... 604/101 |
| 5,171,217 | 12/1992 | March et al. . |
| 5,176,638 | 1/1993 | Don Michael . |
| 5,222,941 | 6/1993 | Don Michael . |
| 5,232,444 | 8/1993 | Just et al. . |
| 5,279,565 | 1/1994 | Klein et al. . |
| 5,282,785 | 2/1994 | Shapland et al. . |
| 5,328,471 | 7/1994 | Slepian . |
| 5,336,178 | 8/1994 | Kaplan et al. . |
| 5,380,284 | 1/1995 | Don Michael . |
| 5,385,548 | 1/1995 | Williams et al. ......................... 604/96 |
| 5,413,557 | 5/1995 | Solar ........................................ 604/96 |
| 5,415,636 | 5/1995 | Forman .................................. 604/101 |
| 5,460,610 | 10/1995 | Michael .................................. 604/101 |
| 5,536,250 | 7/1996 | Klein et al. . |
| 5,569,197 | 10/1996 | Helmus et al. . |
| 5,569,198 | 10/1996 | Racchini . |
| 5,569,215 | 10/1996 | Croker . |
| 5,571,089 | 11/1996 | Croker . |
| 5,575,771 | 11/1996 | Walinsky . |
| 5,779,673 | 7/1998 | Roth et al. .............................. 604/101 |
| 5,800,393 | 9/1998 | Sahota ...................................... 604/96 |
| 5,810,757 | 9/1998 | Sweezer, Jr. et al. ...................... 604/4 |
| 5,819,733 | 10/1998 | Bertram ............................. 128/207.15 |
| 5,836,967 | 11/1998 | Scneider ................................. 606/198 |

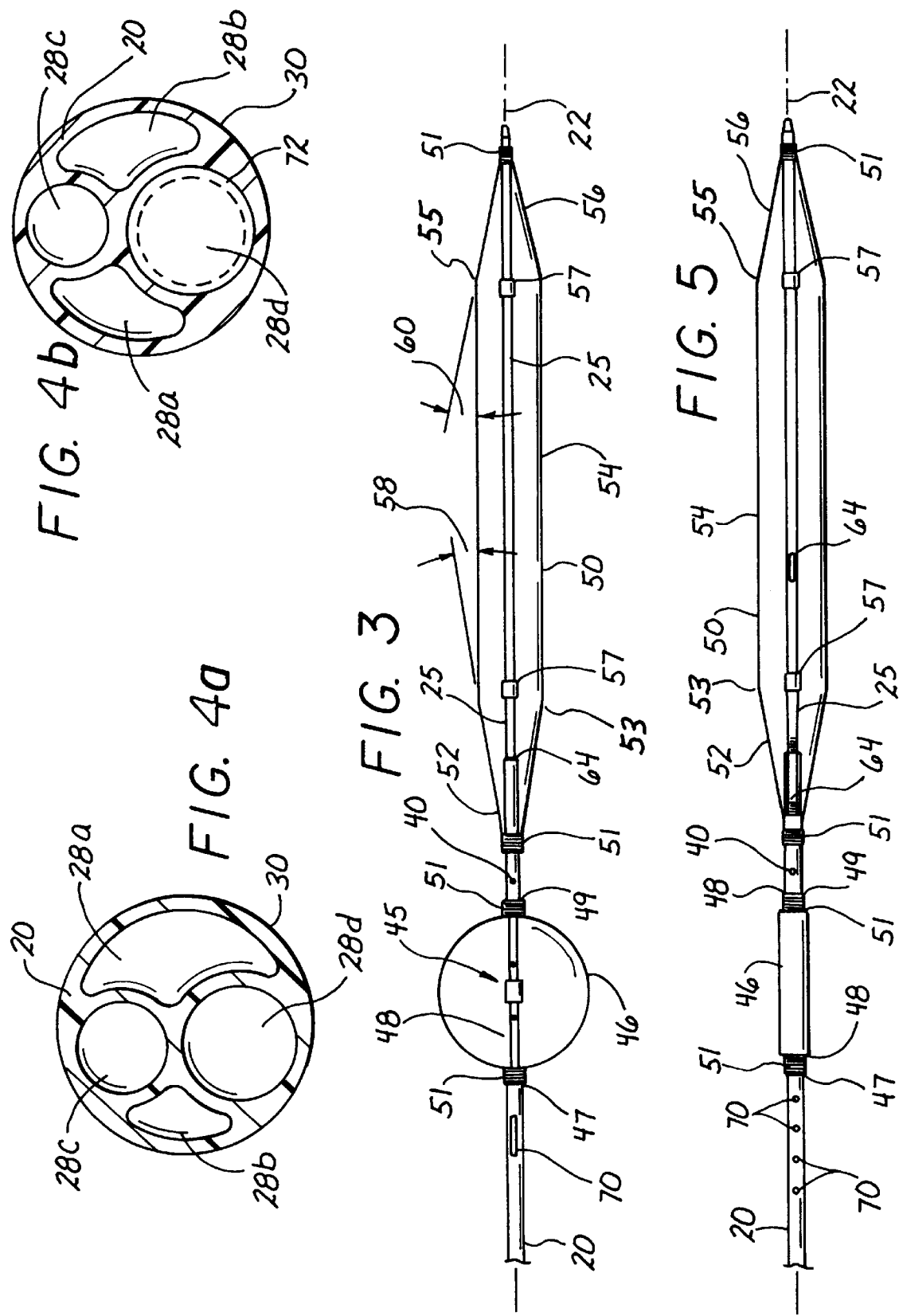

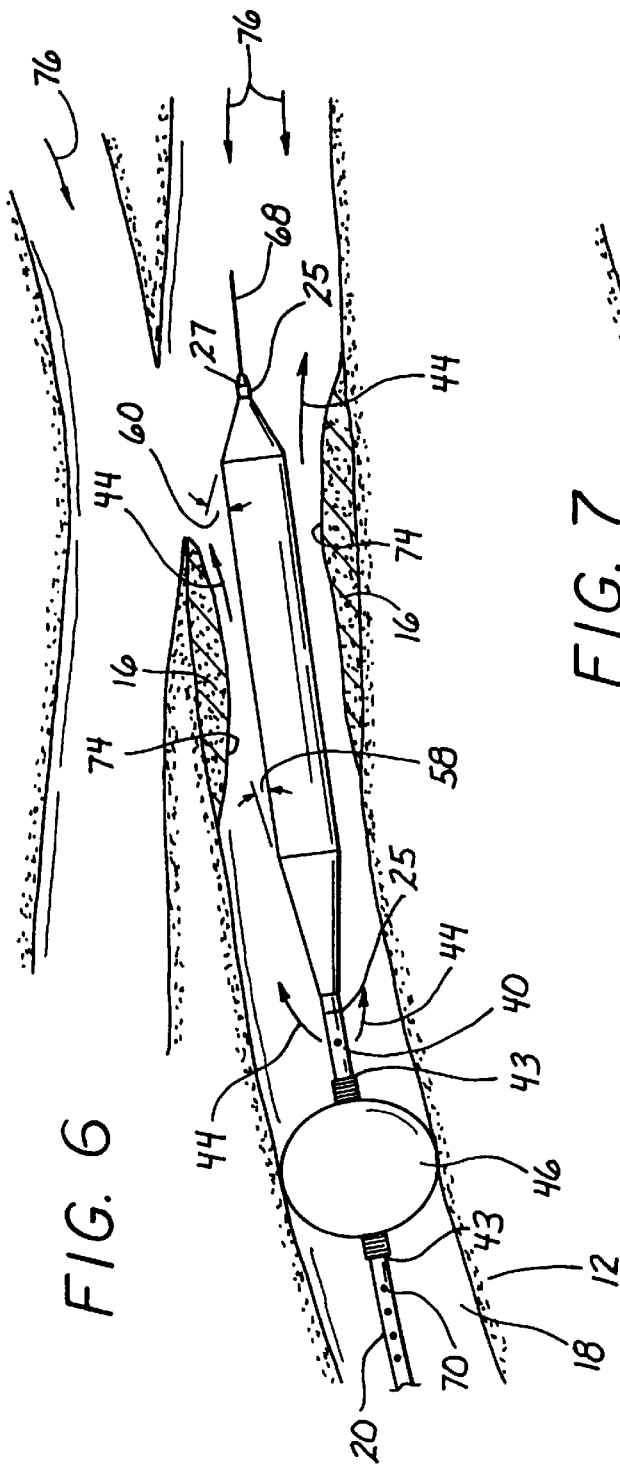
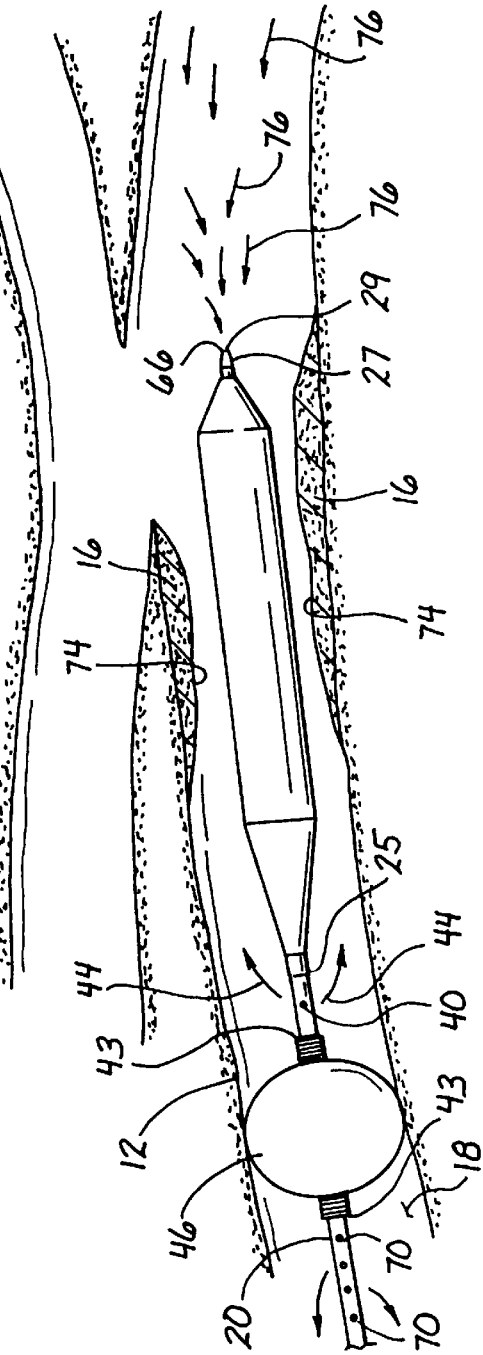

BALLOON CATHETER AND METHOD

FIELD OF THE INVENTION

This invention relates generally to catheters for insertion into a body passageway and more particularly, to a double balloon catheter for angioplasty and for delivery of therapeutic agents within a body passageway.

BACKGROUND OF THE INVENTION

The use of balloon catheters for dilating or otherwise opening vascular or other body conduits and passageways which have been partially or entirely blocked by deposits or other obstructions is generally known. These prior art balloon catheters generally include an elongate shaft having at least one inflatable and deflatable balloon or sleeve disposed on the leading or distal end. The balloon catheter is introduced into the affected blood vessel or other body passageway and the deflated balloon is maneuvered into the blocked or otherwise obstructed flow path. Once positioned, the balloon is inflated to enlarge the passageway and compress the deposits or obstructions against the inner wall of the vessel.

In addition to the physical enlargement of the flow passageway by mechanical displacement of deposits, modem techniques may include the use of therapeutic medicines and agents to treat the obstructed regions. These drugs are typically used to soften, dissolve or even prevent the reoccurrence of the obstruction. As a specific example, it is well known to treat coronary and peripheral blood vessel obstructions caused by the buildup of fibrin, thrombus or plaque by delivering concentrated doses of agents or medications for direct deposition into the lesion and/or vessel wall.

In a typical procedure involving the application of therapeutic agents using a balloon catheter, the catheter, which includes a series of treatment fluid exit holes, is inserted into the obstructed vessel. Once positioned, relatively large amounts of medication are delivered to the lesion site to "dissolve" and "break up" the obstruction while the catheter is slowly advanced, sometimes over the course of several hours. Since the agents can freely mix with the blood or other fluid in the passageway, increased concentrations of the agent may be required to maintain adequate treatment at the constriction. This can increase costs due to the quantity of drug used, plus the extended use of the physician and the laboratory facilities. In addition the entire vascular system or other passageway may be exposed to the agent, causing serious side effects.

Double balloon catheters have been developed in an effort to temporarily isolate the drug at the site of the lesion. These catheters typically feature two inflatable balloons spaced apart along the distal end of the catheter shaft. Between the balloons is located a plurality of exit ports for infusion of the therapeutic agent. In use, the double balloon is advanced within the vascular conduit so that the two balloons span the lesion site and drug is infused while the balloons are inflated. However, this tends to block all circulating blood flow through the vessel during the administration of the drug.

Double balloon catheters have been proposed to combine, in a single device, the ability to perform angioplasty and to deliver drugs to the angioplasty site without first having to remove the catheter. These devices present the potential for reducing the procedure time and cost of the procedure when combination angioplasty and local drug treatment is planned. However, many of the devices are quite complex and intricate, and thus costly to produce.

Further, some dual purpose angioplasty and drug delivery catheters require repositioning of the catheter after the angioplasty procedure in order to properly deliver the drug to the expanded area of the vessel wall. However, speed and accuracy of treatment are highly important in these angioplasty and drug treatment procedures. Thus, there is a need for a combination angioplasty and drug delivery catheter of a less complex design which does not have to be repositioned between the steps of angioplasty of the lesion site and drug delivery to the site.

Another disadvantage of prior art double balloon angioplasty and drug infusion catheters is their limited ability to operate within smaller vessels and conduits. Since these catheters include an elongate shaft or catheter body which contains three or more longitudinal lumens, their overall outer diameters are typically large.

In addition, each of the lumens typically requires a maximum cross-section to maximize their fluid capacity. However, this tends to further enlarge the overall diameter of the catheter shaft. Attempts to minimize this shaft diameter have previously let to concerns about the strength of the shaft. Thus, there is a need for a catheter shaft having enlarged longitudinal lumens within a relatively small diameter shaft. There is also a need for such a catheter device which is capable of safely operating within smaller vessels and passageways.

Yet another disadvantage of the present balloon catheter devices is their limited ability to efficiently transport body fluid and particularly bypass blood flow around the area being treated. Typically, the drug delivery catheter creates a partial occlusion of the passageway which, when combined with the low volume or slower delivery of the therapeutic drugs due to the smaller lumens, reduces their usability during longer drug delivery procedures. This is particularly disadvantageous where the viability of down stream tissue may be affected by long occlusion times. And, catheter devices which are capable of autoperfusion (bypass of blood flow through the catheter's internal structure) have increased catheter body diameters due to the additional or larger required lumens, or parts therein. This larger catheter device is restrictive when attempting to access narrow or highly occluded passageways as well as remote vascular locations. Thus, there is a need for a balloon catheter which allows efficient autoperfusion without substantially increasing the diameter of the deflated catheter device.

Yet another disadvantage of the present balloon catheter devices is their even larger diameter around each of the attached balloons. Presently, where the balloons are attached to the catheter device, the overall catheter diameter is enlarged, making operation within the smaller passageways commonly found in modern angioplasty procedures problematic. Merely reducing the catheter shaft diameter in the area of the attached balloons may reduce the diameter of the internal fluid delivery lumen and further restrict drug delivery and balloon inflation/deflation times. Thus, there is a need for a catheter device capable of insertion and operation within smaller body passageways and also capable of adequate drug volume delivery between the balloons.

SUMMARY

The present invention overcomes the foregoing problems of the past by providing a balloon catheter device for performing angioplasty type treatments in conjunction with drug treatment within narrow vascular conduits or body passageways and even within tightly constricted or occluded passageways. By using a catheter body having a plurality of interior lumens, each having a specific cross-sectional shape and orientation relative to the other lumens, the outer diameter of the catheter body is minimized while fluid flow through the lumens is maximized. The efficient spacing and configuration of the lumens also allows the catheter body to retain its strength within a relatively small outer diameter. The device of the present invention may also be utilized for the treatment of adherent materials such as atherosclerotic plaque, thrombosis, stenosis, occlusions, clots, stones, and other potentially obstructive material from within vascular conduits and other body passageways alone or in conjunction with a drug therapy treatment.

The present invention also satisfies the need for a balloon catheter device which can perform angioplasty procedures and deliver high volumes of therapeutic drugs within a body passageway and which is reliable and relatively inexpensive. By providing a catheter body made from an extruded polymer, the present device utilizes longitudinal lumens having optimized cross sectional configurations and locations to maximize their fluid capacity while minimizing the overall outer diameter of the device. In addition, by providing an infusion port between the cuff and the angioplasty balloon, the balloon catheter device of the present invention delivers the drug directly to the vicinity of the vessel wall area under treatment without the need to construct a more difficult-to-produce porous or textured angioplasty balloon.

The present invention is generally directed to a balloon catheter device for treating a constriction or other obstruction within a vascular or other body passageway. The balloon catheter device includes an elongate, flexible catheter body which extends along a longitudinal axis between a proximal end and a distal end. The distal end includes a necked down portion having a smaller overall outer diameter than that of the proximal end. The distal end terminates in a distal tip.

The elongate catheter body includes an outer wall which surrounds a plurality of interior passageways or lumens which extend along the longitudinal axis from the proximal end. At least one of the lumens extends distally from the proximal end to an infusion port through the outer wall and adjacent the distal end. The plurality of lumens are configured to provide a maximum total volume capacity while retaining a maximum catheter body strength within a minimum catheter body outer diameter. Thus, at least one of the lumens has a cross section relative to the longitudinal axis which is non circular.

In an effort to produce a small diameter catheter body containing a plurality of lumens, and at a reasonable cost, the elongate catheter body is preferably extruded from a polymer. The extruded polymer catheter body is bio-compatible and maintains a minimum outer diameter. Preferably, the polymer is a polyurethane, polyethylene, a Nylon, a PBAX or similar material.

A first inflatable and deflatable balloon is disposed coaxially about the catheter body. This first balloon, which is a high compliance cuff for expanding against the vascular wall, is disposed along the elongate catheter body just proximally from the infusion port. A second lumen extends from the proximal end of the catheter body and is fluidly coupled to this first balloon. A fluid or gas is passed through the second lumen to inflate as well as deflate the first balloon.

A second inflatable and deflatable balloon is disposed coaxially about the catheter body. This second balloon, which is a low compliance angioplasty balloon, is disposed distally about the catheter body and is spaced apart from the first balloon. A third lumen extends from the proximal end of the catheter body and is fluidly coupled to this second balloon. A second fluid is passed through the third lumen to inflate as well as deflate the second balloon.

In another aspect of the present invention, the balloon catheter device further comprises a fourth lumen. This fourth lumen extends from the proximal end of the catheter body to an open tip at the distal end. The fourth lumen is configured for movably supporting a catheter guidewire as well as for passage of a bodily fluid from within the vascular or other body passageway. A perfusion port is disposed on the outer wall of the catheter body proximally from the first balloon. This perfusion port is fluidly coupled to the fourth lumen and is configured such that blood or other body fluid may pass through the fourth lumen between the perfusion port and the open tip. This passage allows the body fluid to bypass the first balloon and the second balloon when the catheter guidewire within the fourth lumen is moved proximally of the perfusion port.

In yet another aspect of the present invention, the angioplasty balloon comprises a proximal balloon end which is attached to the outer wall of the catheter body. The proximal balloon end transitions into a central balloon portion which distally transitions into a distal balloon end. The distal balloon end is attached to the outer wall of the catheter body distally from the proximal balloon end. When the angioplasty balloon is inflated, the proximal balloon end angles outwardly and away from the catheter body to the central balloon portion at a first acute angle. In addition, the distal balloon end angles inwardly from the central balloon portion to the catheter body at a second acute angle. A thin line is wrapped around each of the proximal and distal balloon ends to facilitate their securement to the catheter body. Alternatively, the balloon ends may be secured to the catheter body by adhesive means.

In yet another aspect of the present invention, the elongate catheter body includes a necked down portion having a reduced diameter. This necked down portion extends proximally and distally of the angioplasty balloon. The necked down portion allows the angioplasty balloon to be deflated and maintained within a minimum diameter such that the balloon catheter device may be easily passed through a hemostasis valve and introducer sheath combination using Seldinger techniques, as well as utilized within smaller vascular or other body passageways.

In yet another aspect of the present invention, the balloon catheter device has a first and second balloon as previously described, however, in this aspect, the first balloon is a low compliance angioplasty balloon and the second balloon is a high compliance cuff. This configuration is particularly useful when utilizing the balloon catheter device within a vascular passageway along the direction the body fluid flow.

This invention, together with the additional features and advantages thereof, which is only summarized in the foregoing passages, will become more apparent to those of skill in the art upon reading the description of the preferred embodiments, which follows in the specification, taken together with the following drawings.

BRIEF DESCRIPTION OF THE DRAWINGS

FIG. 3 is an enlarged cross-section view of the distal section of the balloon catheter of FIG. 2 taken distally of lines 3—3;

FIG. 4a is a transverse cross-section view of the catheter body of FIG. 2 taken along lines 4—4;

FIG. 4b is a transverse cross-sectional view showing an alternative configuration of the catheter body as shown in FIG. 4a;

FIG. 5 is a partial side view of an alternative embodiment of a balloon catheter according to the present invention;

FIG. 6 is a diagrammatic view of an embodiment of the balloon catheter of the present invention shown positioned within a vascular conduit;

FIG. 7 is a diagrammatic view of the balloon catheter of FIG. 6 shown with the guidewire retracted to allow for perfusion flow.

DESCRIPTION OF THE PREFERRED EMBODIMENTS

Figure 1:
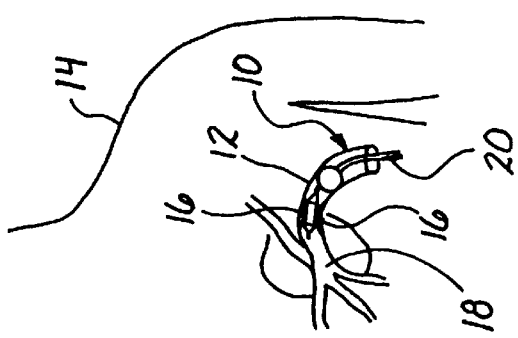
FIG. 1 is a diagrammatic view of an embodiment of the balloon catheter of the present invention shown inside a vascular conduit.
Figure 2:
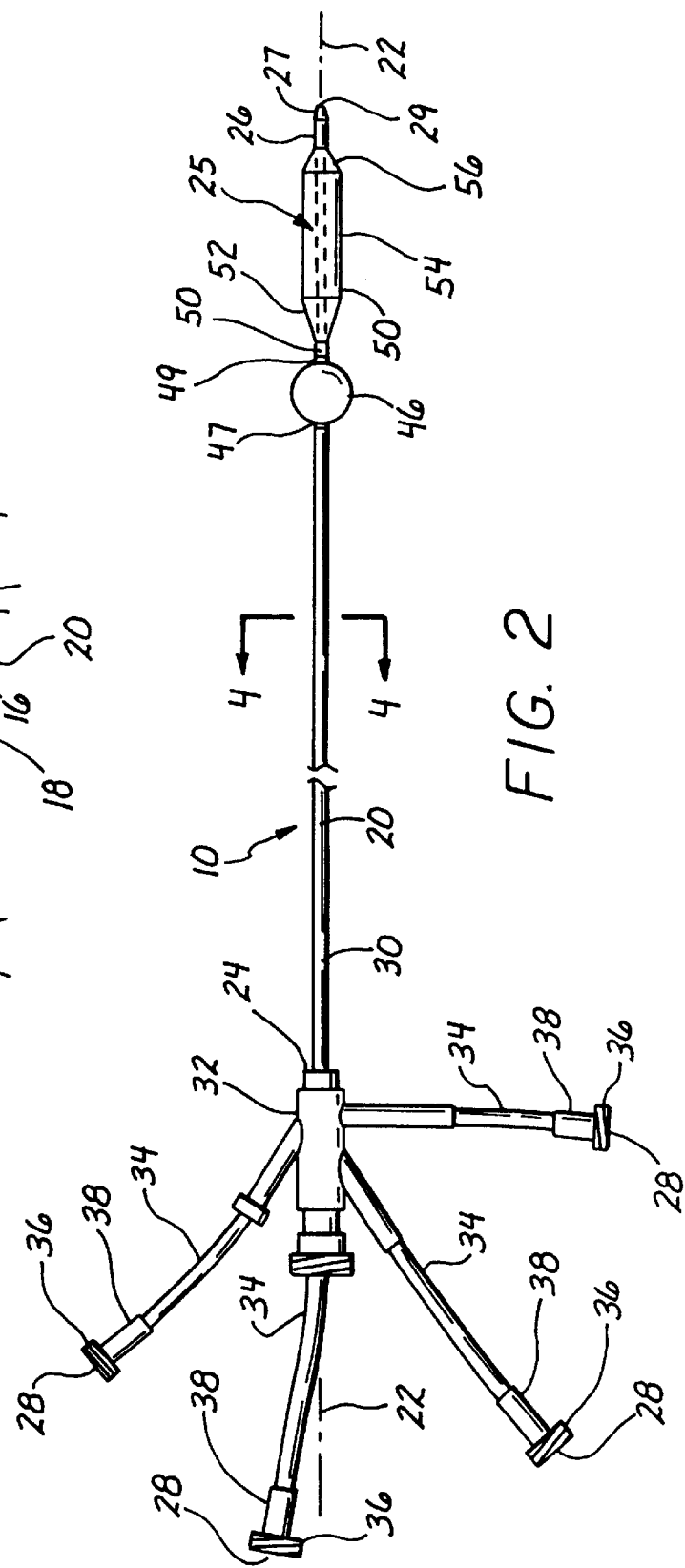
FIG. 2 is a side elevational view of the balloon catheter of the present invention.

Referring now to the drawings, wherein like reference characters designate identical or corresponding parts throughout the several views and embodiments, a balloon catheter device according to the principles of the present invention is illustrated in FIG. 1 and designated by the reference numeral 10. As shown, the balloon catheter 10 is inserted within a body passageway 12 of a patient 14. The body passageway 12 may include almost any body passageway, including a vascular conduit such as an artery, a vessel or a vein. An obstructing material 16 is shown constricting or otherwise obstructing a flow passageway 18 within the body passageway 12. The obstructing material 16 may be a plaque, thrombosis, stenosis, other occlusions, clots, stones, and most any other potentially obstructive material within the vascular conduit or other body passageway 12.

Referring now to FIGS. 2–4b, the balloon catheter device 10 may include an elongate catheter body 20. This catheter body 20 is preferably a flexible tubular shaft having a longitudinal axis 22 extending between a proximal end 24 and a distal end 26. A necked down portion 25 which generally comprises a smaller cross-sectional diameter than the proximal end 24 may be provided at the distal end 26. A plurality of longitudinally aligned interior passageways or lumens 28a, 28b, 28c, and 28d extend along the catheter body from the proximal end 24. An outer surface or wall 30 surrounds the plurality of lumens 28a, 28b, 28c, and 28d and generally defines the elongate catheter body 20, as best illustrated in FIGS. 4a and 4b.

The distal end 26 preferably terminates at a distal tip 27. This distal tip 27 may be an open distal tip with the opening 29 leading into one of the plurality of lumens 28a–28d within the catheter body 20. The distal tip 27 may also be elongate and distally tapered inwardly towards the longitudinal axis 22. The elongate taper improves insertion and manipulation of the balloon catheter device 10 within the body passageway 12

A hub 32 having a plurality of extension tubes 34 may be coupled to the proximal end 24 of the catheter body 20. Each of these extension tubes 34 is preferably connected with a respective one of the plurality of lumens 28a–28d, such that each lumens 28a–28d is fluidly coupled or otherwise in open communication with an extension tube 34. A connecter 36, such as a luer lock, may be provided at a proximal end 38 of each extension tube 34. The hub 32, which may be a quadfurcated hub, is coupled to the proximal end 24 of the catheter body 20 as is known to those of skill in the art.

Strain reliefs may also be incorporated between the hub 32 and the catheter body 20 to prevent kinking and possible restrictions within one or all of the plurality of lumens 28a–28d during manipulation of the balloon catheter device 10.

An infusion port 40 may be provided within the outer wall 30. This infusion port 40 is preferably fluidly coupled to an infusion lumen 28a, which preferably comprises one of the plurality of lumens 28a–28d. The infusion port 40 and infusion lumen 28a may be used to pass a medicine or drug 44, such as a therapeutic agent, from a supply attached to one of the connectors 36 and thus, to the catheter body 20 and the body passageway 12 through the interconnected hub 32, as best illustrated in FIG. 6. Preferably, the infusion port 40 is a single oval shaped port, but the port 40 may be a different shape, such as circular, if desired. The relatively large infusion port 40 is also advantageous when the drug is a viscous treatment fluid 44. The infusion port 40 may also comprise a plurality of spaced apart openings or ports. These plurality of ports may be desirable for increased flow. The drug 44 may comprise heparin, urokinase, horseradish peroxidase, or other therapeutic agents including antiplatlet, antithrombin, thrombolytic, calcium blocking, steroidal, for example, as well as tissue antiproliferative and proliferative agents.

It is often desirable to infuse a relatively large quantity of the drug 44 or other liquid therapy into the body passageway 12 within a relatively short period of time, typically over a few seconds or minutes. Thus, the infusion lumen 28a should comprise a sufficiently large cross sectional area along the catheter body 20 to allow for passage of a large volume of the drug 44, including a highly viscous fluid.

The infusion lumen 28a may have a non circular cross section, as best illustrated in FIGS. 3 and 4, which may allow for a maximum cross sectional area along the longitudinal axis 22. This non circular cross section may be optimally configured to fit adjacent to the remaining plurality of lumens 28a–28d to maximize the total volume capacity of the plurality of lumens 28a–28d, while minimizing the overall outer diameter of the catheter body 20 and particularly the outer wall 30. The non circular cross section may preferably be generally triangular in shape with rounded outer boundaries. The infusion lumen 28a may also be configured with a circular, oval, square, trapezoidal, rhomboidal, or any other shaped cross section.

A first inflatable and deflatable balloon 46 having disposed coaxially about the catheter body 20. This first balloon 46, which is preferably a high compliance balloon, is disposed along the elongate catheter body 20 just proximal of the infusion port 40. The first balloon 46 may be used for expanding against the body passageway 12 and anchoring or immobilizing the balloon catheter 10 in a desired location. The first balloon 46 may also be used to seal against the body passageway 12 and block the flow of a body fluid, such as blood flow within an artery or vessel. Preferably, the first balloon 46 is configured such that it expands uniformly to place a constriction or seal along the circumferential section of the body passageway 12. In addition, the first balloon 46 provides many additional advantages, such as preventing the migration of clots or any other fragments of the obstructing material 16 from traveling along the flow pathway 18 past balloon 46.

The first balloon 46 may be a round or semi-round balloon having a proximal end 47 and a distal end 49. The balloon 46 is preferably made from a flexible and bio-compatible material. These materials may include a rubber such as a medical grade latex, a silicone and even polyurethane. The proximal and distal ends 47 and 49 of the first balloon 46 may be attached to the catheter body 20 using an adhesive, such as a cyanoacrylate-based adhesive, a heat set bonding process or any other method as is known to those in the construction of balloon catheters. A thin line 51 may also be wrapped around each of the first balloon ends 47 and 49 to ensure a tight fit and prevent leakage. This thin line 51, which may be a suture material, may include a monofilament line, a braided line or any other thin line capable of maintaining the balloon ends 47 and 49 scaled against the catheter body 20.

The first balloon 46 may also be attached to a second necked down portion 48 of the catheter body 20 which has a smaller or reduced cross sectional diameter along the longitudinal length of the shaft 20. This second necked down portion 48 may be located between the first proximal and distal balloon ends 47 and 49. However, the first balloon 46 may be made and attached to the catheter body 20 in any way and configuration which allows sufficient expansion to seal around the flow passageway 18 or alternatively act as an anchor within the passageway 18. A platinum or other marker band 45 may be placed under the first balloon 46 or the catheter shaft 20 adjacent to the first balloon 46 to identify the location of the first balloon once inserted within the patient 14.

A second lumen 28b of the plurality of lumens 28a–28d extends from the proximal end 24 of the catheter body 20 and is fluidly connected to an opening or openings in the outer wall 30 within the first balloon 46. A fluid or a gas is passed through this second lumen 28b to inflate as well as deflate the first balloon 46. Preferably, this fluid or gas is air which is passed through the second lumen 28b at a pressure sufficient to expand the first balloon 46 against the body passageway 12 without damage to the endothelium, which pressure is preferably less than two atmospheres. Similarly to the infusion lumen 28a, the second lumen 28b may comprise a non circular cross section as it extends along the catheter body 20, such as a generally triangular cross section.

A second inflatable and deflatable balloon 50 is also disposed coaxially about the catheter body 20. This second balloon 50 is preferably elongate relative to the first balloon 46 and includes a proximal balloon end 52, a central balloon portion 54 and a distal balloon end 56. The second balloon 50 is preferably a low compliance angioplasty balloon and preferably made from a tough, thin-walled thermoplastic tubing or other similar material, as is generally known to those of skill in the art of angioplasty. The second balloon 50 is preferably disposed on the first necked down portion 25 of the catheter body 20 and spaced distally from the first balloon 46. The necked down portion 25, similar to the second necked down portion 48, is configured to allow the balloon 50 to deflate and fold down into a minimum diameter profile for passage through the body passageway 12.

In the presently described configuration, the proximal balloon end 52 of the angioplasty balloon 50 is attached to the catheter body 20 distally and spaced apart from the infusion port 40. The attachment of the proximal and distal ends 52 and 56 to the catheter body 20 may be accomplished using conventional means and methods, such as heat bonding, epoxy bonding, use of other adhesives, such as a cyanoacrylate or cyanoacrylate-based adhesive, or the like and as are known to those of skill in the art of manufacturing balloon catheters. Similarly to that described for the first balloon 46, a thin line 51 may be wrapped around the proximal end 52 and the distal end 56 to ensure a strong fit and prevent leakage.

Locator markers 57, such as one or more platinum marker bands or a radio opaque band, may be placed about the catheter body 20 adjacent to the second balloon 50. Preferably, the locator markers 57 include a pair of spaced apart platinum bands attached to the catheter body 20 under the balloon 50, one at a proximal balloon shoulder 53 and the other at a distal balloon shoulder 55. These markers 57 may be used to identify the effective area of vessel contact of the second balloon 50 and to assist in manipulating the catheter device 10 within the body passageway 12, such as with fluoroscopy. These locator markers 57 may be identical to locator markers 45.

When the second balloon 50 is expanded, the proximal balloon end 52 angles outwardly and away from the catheter body 20 and into the central balloon portion 54 at a first acute angle 58. In addition, the distal balloon end 56 angles inwardly from the central balloon portion 54 to the catheter body 20 at a second acute angle 60. Preferably, each of the first and second acute angles 58 and 60 is between approximately 5 and 45 degrees and more preferably between approximately 10 and 20 degrees. The first acute angle 58 and the second acute angle 60 may be generally the same, as best illustrated in FIG. 3 or may be different, as best illustrated in FIG. 6.

A third or angioplasty balloon inflation lumen 28c, of the plurality of lumens 28, extends through the catheter body 12 from the proximal end 24 to a second balloon inflation port 64 within the second balloon 50. A second fluid may be passed through this third lumen 28c to inflate as well as deflate the second balloon 50. Preferably, this second fluid is a sterile saline solution or water, combined with an equal volume of radiographic contrast solution. However, any fluid or gas capable of inflating and deflating the second balloon 50 may be used, including fluids and gases containing medicines or radioactive substances used to irradiate the vessel wall to reduce restenosis.

The third lumen 28c should have a sufficiently large cross-section along the catheter body 20 to allow for a complete deflation of the second balloon 50 in a relatively short period of time, preferably 10 seconds or less. If the cross section of the third lumen 28c is too small, the second balloon 50 may not fully deflate, causing difficulty when attempting to move or even withdraw the catheter device 10 and may potentially pose a safety risk to the patient 14. This is especially true when using a more viscous fluid to inflate and deflate the balloon 50. Preferably, the third lumen 28c comprises a circular cross section along the length of the catheter body 20, but may alternatively be configured with a non-circular cross section.

A fourth lumen 28d, of the plurality of lumens 28a–28d, may extend through the catheter body 20. The fourth lumen 28d, which preferably extends from the proximal end 24 through the open distal tip 27, may be configured for movably supporting a catheter guidewire 68 as well as for passage of a body fluid or contrast solution from within, or into, the body or vascular passageway 12. As such, the fourth or "guidewire" lumen 28d should be of a large enough cross section along the entire catheter body 20 to accommodate the circumference of the catheter guidewire 68. Preferably, the guidewire lumen 28d has a cross section which is generally circular in shape for use with a guidewire having a generally circular cross section. However, different cross section shapes may be used, particularly if a guidewire having a non circular shape is used, or it is desired to pass fluid through the lumen when the guidewire is in place. The guidewire 68 may be passed through the fourth or guidewire lumen 28d and used to insert and direct the balloon catheter device 10 into the patient 14 as is known to those in the art of catheterization of body lumens.

An autoperfusion port 70 (FIG. 3) may be disposed on the outer wall 30 of the catheter body 20 proximally of the first balloon 46. This perfusion port 70, which may include a plurality of oval or circular shaped ports aligned along the longitudinal axis 22 and disposed proximal to the first balloon 46, as best illustrated in FIG. 5, is fluidly coupled to the guidewire lumen 28d. The ports 70 are configured such that a fluid within the body passageway 12 may pass through the guidewire lumen 28d between the perfusion port 70 and the open distal tip 27 at a higher flow rate when the guidewire 68 is moved proximally of the port 70. A seal 72 may be provided within the guidewire lumen 28d to movably support the guidewire 68 and to restrict fluid flow (FIG. 4b). The seal 72 may be disposed proximally of the perfusion port 70 to prevent any fluid from moving within the guidewire lumen 28d proximally of the perfusion port 70. Alternatively, the seal 72 may be provided directly on the distal end of the guidewire 68.

By moving the guidewire 68 within the guidewire lumen 28d such that it is proximal to the perfusion port 70, fluid within the body passageway can bypass the first balloon 46 and the second balloon 50 at a higher flow rate. For example, when the balloon catheter device 10 is used within a vascular conduit, the guidewire 68 may be moved within the guidewire lumen 28d such that it is proximal to the perfusion port 70. This allows blood to flow through the guidewire lumen 28d between the opening 29 in the distal tip 27 and the perfusion port 70, and to bypass the first and second balloons 46 and 50. This is particularly important when downstream tissue requires the otherwise restricted blood or other body fluid.

Preferably, the catheter body 20 comprises an outer diameter which is minimized. Minimizing this outer diameter allows utilization of the balloon catheter device 10 within small vascular conduits and body passageways 12 as well as in very occluded passageways 12. However, as previously discussed, at least some of the plurality of lumens 28a–28d are preferably configured with a maximum sized cross section along the catheter body 20. In particular, the plurality of lumens 28a–28d are preferably configured to provide a maximum total fluid flow capacity while retaining a maximum strength in the catheter body 20 and within a minimum diameter catheter body 20.

To enable the diameter of the catheter body 20 to be minimized while the cross sectional area of each lumen 28a–28d is maximized, at least one of the lumens 28a–28d is provided with a non circular shaped cross section relative to the longitudinal axis 22. For example, when using a catheter body 20 having a generally circular cross section, two of the lumens 28a–28d may be of a generally circular cross sectional shape and the other two lumens 28a–28d may be configured with a cross section shaped like a generally rounded triangle. The triangular shape efficiently utilizes the cross sectional area between the two circular lumens 28a–28d without yielding substantial strength of the catheter body 20. Thus, lumen cross sections having any shape may be utilized.

Referring now in particular to FIGS. 4a and 4b, the plurality of lumens 28a–28d may be generally symmetrical in cross section size. Particularly, the guidewire lumen 28d and the third, or angioplasty balloon lumen 28c may be circular in cross section with the guidewire lumen 28d typically requiring the largest, and a fixed size, cross section. The first or infusion lumen 28a and the second or cuff inflation lumen 28b may be similar in size and both non circular in cross sectional shape. This configuration may be preferable to balance the torsional characteristics of the catheter body 20 so that the bending characteristics and thus the maneuverability is balanced. In addition, this configuration may be simpler and less expensive to extrude. Alternatively, the catheter body 20 may be configured having one of the plurality of lumens 28a–28c, and preferably the infusion lumen 28a, enlarged with respect to the remaining lumens 28b–28c, as best illustrated in FIG. 4b. This configuration may be preferred where large volumes of the drug 44 or alternatively viscous drugs 44 are to be delivered.

The catheter body 20 may be extruded from a polymer. Such a polymer may include polyurethane, a nylon, a polyethylene, a PBAX, other plastic, or any other material which is generally bio-compatible and may be extruded as an elongate shaft. Alternatively, any materials and techniques of construction may be used to build the present catheter body 20.

Figure 8:
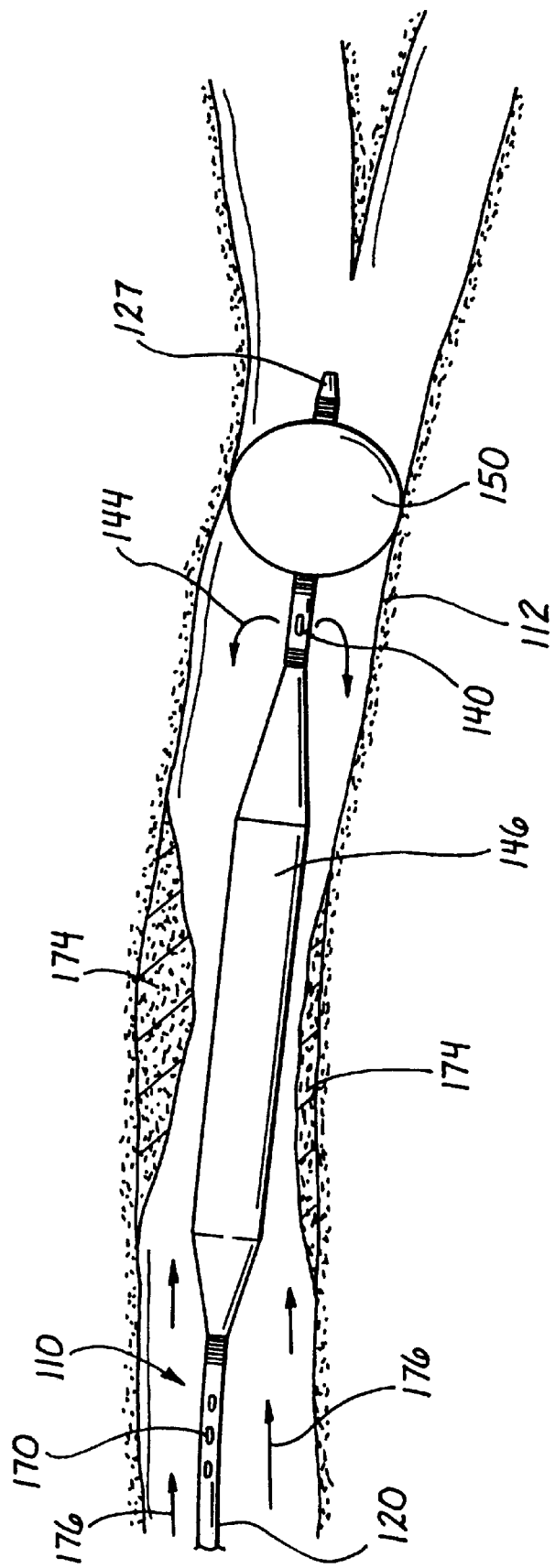
FIG. 8 is a partial side view of an alternative embodiment of a balloon catheter according to the present invention.

Referring now to FIG. 8, a second alternative embodiment of a balloon catheter constructed in accordance with the principles of the present invention is shown. In this embodiment, like features to those of previous embodiments are designated by like reference numerals, preceded by the numeral 1. The balloon catheter device 110 includes a high compliance balloon 150 and an angioplasty balloon 146 as previously described, but they are reversed in location along the catheter body 120. In this embodiment, the first or proximal balloon 146 is a low compliance angioplasty balloon and the second or distal balloon 150 is a high compliance cuff. This configuration is particularly useful when utilizing the balloon catheter device 110 within a vascular or other body passageway 112 wherein the catheter is advanced along the flow direction of the body fluid 176.

Referring now to FIGS. 1 through 8, a method of using a balloon catheter device, such as the balloon catheter device 10 of the present invention will be described. The method, which treats a constriction 74 (FIGS. 6 and 7), including an obstructing material 16, such as a body plaque, within a vascular conduit or other body passageway 12, includes the step of providing a balloon catheter device such as the balloon catheter device 10 previously described. The provided balloon catheter device 10 includes an elongate catheter body 20 on which a high compliance balloon or cuff 46 and a low compliance angioplasty balloon 50 are each coaxially disposed. The catheter body 20 supports a plurality of lumens 28a–28d which extend along the catheter body 20 from a proximal end 24. At least one of the lumens 28a–28d has a non-circular cross section along the catheter body 20.

The provided balloon catheter device 10 is inserted into the vascular conduit 12 such that the angioplasty balloon 50 is located within the constriction 74. This insertion step may include passing a catheter guidewire 68 through a guidewire lumen 28d within the catheter body 20 to direct the catheter device 10 along the body passageway 12.

Once the angioplasty balloon 50 is positioned within the constriction 74 of the conduit 12, it is inflated. Inflation may include using a pressurized fluid or gas which is passed through an angioplasty balloon lumen 28c within the catheter body 20. Preferably, the balloon 50 is inflated with a saline solution or water. The angioplasty balloon 50 is preferably inflated to a relatively high pressure, sufficient to remodel the constriction 74 and partially flatten the obstructing material 16 against or into the walls of the body conduit 12. The angioplasty balloon 50 is then deflated and the inflation/deflation process may be repeated. These steps may comprise various other and differing steps as used with the various techniques of angioplasty and as is known to those in the art of angioplasty.

To deliver a drug or other therapeutic agent 44 to the remodeled constriction 74, the angioplasty balloon 50 is again inflated. This inflation is preferably only sufficient to fill the balloon 50 so that it contacts the vessel wall. Alternatively, the angioplasty balloon 50 may be deflated or only partially inflated.

The high compliance balloon 46 is then inflated. This step of inflating the high compliance balloon 46 may be achieved by passing a pressurized gas or fluid through a balloon inflation lumen 28b. Preferably, relatively low pressure air is used. Generally, 2 ATM or less is sufficient. The high compliance balloon 46 may be inflated to anchor the catheter device 10 within the body passageway 12 as well as to prevent a fluid 76, such as blood or any other body fluid, from moving beyond the balloon 46.

A drug 44 or other therapeutic agent may then be passed through an infusion lumen 28a of the plurality of lumens 28a–28d, exiting from an infusion port 40 disposed between the high compliance balloon 46 and the angioplasty balloon 50 on the catheter body 20. The drug 44 may be infused at a pressure greater than the pressure within the angioplasty balloon 50 but less than the pressure within the high compliance balloon 46. This allows the drug 44 to exit the infusion port 40 into the sealed space between the high compliance balloon 46 and the angioplasty balloon 50. The drug 44 may then seep around the angioplasty balloon 50 which is sufficiently inflated to be in contact with the body passageway 12. Seepage may also occur within interstices, cracks and tears in the walls of the obstructing material 16 and the body passageway 12. In this configuration, the drug 44 is uniformly applied at a uniform pressure to the surface of the body passageway 12 but preferentially flows into any cracks, depressions, or tears within the body passageway 12 or obstructing material 16.

As previously mentioned, the angioplasty balloon 50 may also be partially deflated during infusion of the drug 44. This creates a space over and across the angioplasty balloon 50 into which the body fluid 76 may flow. In this configuration, the drug 44 as well as the body fluid 76, are more rapidly intermixed in the area of the constriction 74, and some of the drug 44 may be forced to flow toward the tip of the catheter, thus treating areas of the vessel walls in smaller regions more distal to the catheter. Alternatively, both the angioplasty balloon 50 and the cuff 46 may be partially or fully deflated and the catheter device 10 may be repositioned within the body conduit 12. The drug 44 may then be infused and allowed to flow freely across the high compliance and angioplasty balloons 46 and 50 with the body fluid 76. After repositioning, the first and second balloons 46 and 50 may be reinflated and the drug 44 infused only into the vessel wall area 12 between the two balloons.

The method may include the step of moving the guidewire 68 proximally within a guidewire lumen 28d to activate the autoperfusion port 70. This is particularly useful when infusing the drug 44 for a relatively long period of time and where tissue downstream may be otherwise injured due to the lack of body fluid 76 flow such as blood.

After treatment is completed, the high compliance balloon 46 and the angioplasty balloon 50 may each be deflated and the balloon catheter device 10 removed from within the body passageway 12. The tapered ends 52 and 56 of the angioplasty balloon 50 and the retraction (deflation) and refolding of the balloons 46 and 50 into the neck down areas 25 and 48 of the catheter body 20 assist in smooth and speedy retraction of the catheter 10 from the body conduit 12.

In a minor variation of the above described method as best illustrated in FIG. 8, the balloon catheter device 110 is inserted into the body passageway 112 upstream of the constriction 174. In this embodiment, the method includes providing a balloon catheter device 110 having the first or proximal balloon 146 which is the angioplasty balloon and the second or distal balloon which is the high compliance balloon or cuff 150. Thus, the high compliance balloon 146 is still used to block the body fluid 176 upstream of the angioplasty balloon 150. Thus, a rapid intermixing of the drug 144 exiting the infusion ports 140 with the body fluid 176, causes a uniform treatment of the vessel or other body passageway walls 112.

It will be understood that various modifications can be made to the embodiments of the present invention herein disclosed without departing from the spirit and scope thereof. For example, various sizes of the balloon catheter device and particularly, the catheter body, are contemplated as well as various types of construction materials. Also, various modifications may be made in the configuration of the parts and their interaction. Therefore, the above description should not be construed as limiting the invention, but merely as an exemplification of preferred embodiments thereof. Those of skill in the art will envision other modifications within the scope and spirit of the present invention as defined by the claims appended hereto.

What is claimed is:

1. A balloon catheter device for treating an obstructing material within a body passageway, said device comprising:
   an elongate, flexible catheter body having a longitudinal axis extending between a proximal end and a distal end, said catheter body further comprising an outer wall and a plurality of lumens extending along said longitudinal axis from said proximal end, at least one of said lumens extending to an infusion port in said outer wall, said infusion port being disposed adjacent the distal end;
   a first inflatable and deflatable balloon, disposed coaxially about the catheter body proximally of the infusion port, said first balloon being in fluid communication with a second of said plurality of lumens for inflation and deflation of said first balloon; said
   a second inflatable and deflatable balloon disposed coaxially about the catheter body distally and spaced apart from said first balloon, distally of the infusion port, said second balloon being in fluid communication with a fourth of said plurality of lumens for inflation and deflation by passage of a second fluid;
   one of said first and second balloons comprising a high compliance cuff and the other comprising a low compliance angioplasty balloon;
   wherein there is no balloon disposed between said infusion port and said low compliance cuff.

2. The balloon catheter device as recited in claim 1, and further comprising:
   at least one perfusion port disposed on the outer wall of the catheter body proximally of the first balloon, said perfusion port being in fluid communication with the fourth lumen;
   wherein a bodily fluid within the body passageway may pass through said fourth lumen between said perfusion port and said open tip and bypass said first balloon and said second balloon when the catheter guidewire in said fourth lumen is moved proximally of said perfusion port.

3. The balloon catheter device as recited in claim 2, wherein said fourth lumen comprises a seal disposed proximally of said perfusion port, said seal being configured for movably supporting said catheter guidewire and for preventing the passage of fluid.

4. The balloon catheter as recited in claim 1 wherein said catheter body comprises an extruded polymer.

5. The balloon catheter as recited in claim 4 wherein said polymer comprises a polyurethane, polyethylene, a Nylon or a PBAX.

6. The balloon catheter device as recited in claim 1 wherein said first balloon is a high compliance cuff and said second balloon is a low compliance angioplasty balloon.

7. The balloon catheter device as recited in claim 1 wherein said second balloon is a high compliance cuff and said first balloon is a low compliance angioplasty balloon.

8. A balloon catheter device for treating an obstructing material within a body passageway, said device comprising:
    an elongate, flexible catheter body having a longitudinal axis extending between a proximal end and a distal end, said catheter body further comprising an outer wall and at least four lumens extending along said longitudinal axis from said proximal end, a first of said four lumens extending to an open distal tip at the distal end and being configured for movably supporting a catheter guidewire, a second of said lumens extending to an infusion port within said outer wall, said infusion port being disposed adjacent the distal end;
    a first inflatable and deflatable balloon disposed coaxially about the catheter body proximally of the infusion port, said first balloon being in fluid communication with a third of said plurality of lumens for inflation and deflation by passage of a fluid; and
    a second inflatable and deflatable balloon disposed coaxially about the catheter body distally and spaced apart from said first balloon, distally of the infusion port, said second balloon being in fluid communication with a fourth of said plurality of lumens for inflation and deflation by passage of a second fluid;
    one of said first and second balloons comprising a high compliance cuff and the other comprising a low compliance angioplasty balloon;
    wherein there is no balloon disposed between said infusion port and said low compliance cuff; and
    wherein at least one of said plurality of lumens has a non-circular cross-section.

9. The balloon catheter device as recited in claim 8 wherein said angioplasty balloon comprises a proximal balloon end which is attached to said catheter body and, when inflated, tapers away from said longitudinal axis at a first acute angle to a central balloon portion, said central balloon portion tapering at a second acute angle to a distal balloon end which is attached to said catheter body distally from said proximal balloon end.

10. The balloon catheter device as recited in claim 8 wherein said first acute angle and said second acute angle are different.

11. The balloon catheter device as recited in claim 9 wherein one of said angioplasty balloon and said high compliance cuff are attached to a necked down portion of said catheter body.

12. The balloon catheter device as recited in claim 8 wherein said open distal tip is tapered inwardly toward the longitudinal axis.

13. The balloon catheter device as recited in claim 8 wherein said first lumen and at least one of said third and fourth lumens each have a generally circular cross section.

14. The balloon catheter device as recited in claim 8 wherein said second lumen and at least one of said third and fourth lumens each have a generally rounded triangular cross section.

15. The balloon catheter device as recited in claim 8, and further comprising a radiolucent marker located under the angioplasty balloon.

16. The balloon catheter device as recited in claim 8 wherein said catheter body comprises an extruded polymer.

17. The balloon catheter device as recited in claim 8 wherein said high compliance cuff comprises a proximal balloon end and a distal balloon end and wherein at least one of said proximal and distal balloon ends is secured to said catheter body using a thin filament.

18. The balloon catheter device as recited in claim 8 wherein said high compliance cuff comprises a proximal balloon end and a distal balloon end and wherein at least one of said proximal and distal balloon ends is secured to said catheter body using a cyanoacrylate adhesive.

19. A method for relieving a constriction in a vascular conduit using a balloon catheter device having an elongate catheter body extending along a longitudinal axis between a proximal catheter end and a distal catheter end, a high compliance cuff and a low compliance angioplasty balloon being disposed coaxially about the distal end of said catheter body, said method comprising the steps of:
    inserting the balloon catheter device into the vascular conduit such that said angioplasty balloon is within said constriction;
    inflating said low compliance angioplasty balloon within said vascular conduit;
    inflating said high compliance cuff within said vascular conduit;
    infusing a therapeutic agent through a lumen in said catheter and out of an infusion port disposed on said catheter body between said high compliance cuff and said angioplasty balloon;
    partially deflating said angioplasty balloon so that the therapeutic agent flows over said constriction in order to more effectively treat said constriction.

* * * * *